United States Patent [19]

Taylor et al.

[11] Patent Number: 6,133,240
[45] Date of Patent: Oct. 17, 2000

[54] TETRAHYDRONAPTHALENE DERIVATIVES AND THEIR THERAPEUTIC USE

[75] Inventors: Richard John Kenneth Taylor, York, United Kingdom; Paul Vincent Murphy, Dublin, Ireland; John Gary Montana; David Thomas Manallack, both of Cambridge, United Kingdom

[73] Assignee: Darwin Discovery, Ltd., United Kingdom

[21] Appl. No.: 08/924,688

[22] Filed: Sep. 5, 1997

[30] Foreign Application Priority Data

Sep. 5, 1996 [GB] United Kingdom ............... 9618520

[51] Int. Cl.⁷ ............... A61K 31/70; C07H 15/00
[52] U.S. Cl. ............... 514/25; 536/4.1; 536/17.9
[58] Field of Search ............... 536/4.1, 17.9; 514/25

[56] References Cited

FOREIGN PATENT DOCUMENTS 9619231   6/1996   WIPO .

OTHER PUBLICATIONS

Singh, Sheo Bux, and George R. Pettit (Oct., 1990) "Antineoplastic Agents, 195. Isolation and Structure of Aceratioside From *Aceratium megalopsermum*" Journal of Natural Products, 53(5):1055–1397.

Paulson "Carbohydrate Ligands of Leukocyte Adhesion Molecules and Their Therapeutic Potential" in *Progess in Brain Research* 1994, 101, 179–184, Chapter 13. Months not available.

Levy et al. "Cell Adhesion and Carbohydrates" in *Annual Reports in Medicinal Chemistry* 1994, 29, 215–224, Chapter 22. Month is not available.

*Primary Examiner*—Kathleen K. Fonda
*Attorney, Agent, or Firm*—Saliwanchik, Lloyd & Saliwanchik

[57] ABSTRACT

Compounds of the formula

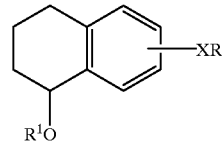

(I)

wherein $R^1$ is a fucose or mannose residue, have therapeutic utility via inhibition of selectins, and thus of cell adhesion.

12 Claims, No Drawings

TETRAHYDRONAPTHALENE DERIVATIVES AND THEIR THERAPEUTIC USE

FIELD OF THE INVENTION

This invention relates to tetrahydronapthalene derivatives and their therapeutic use. The compounds inhibit cell adhesion via inhibition, for example, of E, L and/or P-Selectin.

BACKGROUND OF THE INVENTION

A large body of data has been accumulated that establishes a role for a family of receptors, the selectins (hereinafter LEC-CAMS), in certain diseases including cancer, autoimmunity, and in the inflammatory response. The three known members of this family, L-Selectin (LECAM-1, LAM-1, gp90MEL), E-Selectin (LECAM-2, ELAM-1) and P-Selectin (LECAM-3, GMP-140, PADGEM), each contain a domain with homology to the calcium-dependent lectin (C-lectins), an EGF-like domain, and several complement-binding protein-like domains (Bevilacqua et al, Science (1989) 243:1160–1165; Johnston et al, Cell (1989) 56:1033–1044; Lasky et al, Cell (1989) 56:1045–1055; Tedder et al, J. Exp. Med. (1989) 170:123–133). It has been proposed that the selectins bind to particular ligands and that this accounts for their biological activity. Thus, drugs that interfere with or prevent binding of the ligands to the selectins will be useful medicaments for treating a variety of diseases.

For instance, adhesion of circulating neutrophils to stimulated vascular endothelium is a primary event of the inflammatory response. P-selectin has been shown to be centrally involved, particularly as related to acute lung injury. Mulligan et al, J. Clin. Invest. (1991) 90: 1600, report strong protective effects using anti-P-selectin antibody in a rodent lung injury model.

Of the three selecting, ELAM-1 is particularly interesting because of its transient expression on endothelial cells in response to IL-1 or TNF (Bevilacqua et al, supra). The time course of this induced expression (2–8 h) suggests a role for this receptor in initial neutrophil extravasation in response to infection and injury. Indeed, Gunel et al, J. Clin. Invest. (1991) 88:1407, have shown that antibody to ELAM-1 blocks the influx of neutrophils in a primate model of asthma and thus is beneficial for preventing airway obstruction resulting from the inflammatory response.

Lowe et al, Cell (1990) 63:475, demonstrated a positive correlation between ELAM-1-dependent adhesion of HL-60 cell variants and transfected cell lines, with their expression of the sialyl Lewis x (sLe$^x$) oligosaccharide, Neu NAc α2-3Gal-β1-4(Fuc α1-3)-GlcNAc. By transfecting cells with plasmids containing an α(1,3/1,4) fucosyltransferase, they were able to convert non-myeloid COS or CHO lines into sLe$^x$-positive cells that bind in an ELAM-1 dependent manner. Walz et al, Science 250 (4984):1132 (1990) were able to inhibit the binding of a ELAM-1-1gG chimera to HL-60 cells with a monoclonal antibody directed against sLe$^x$ or by glycoproteins with the sLe$^x$ structure, but could not demonstrate inhibition with CD65 or CD15 antibodies. Both groups concluded that the sLe$^x$ structure is the ligand for ELAM-1.

ELAM-1 is a glycoprotein that is found on the surface of endothelial cells, the cells that line the interior wall of capillaries. E-selectin recognises and binds to sLe$^x$, which is present on the surface of certain white blood cells. E-selectin helps white blood cells recognise and adhere to the capillary wall in areas where the tissue surrounding the capillary has been infected or damaged. P-selectin is expressed on inflamed endothelium and platelets, and has much structural similarity to E-selectin and can also recognise sLe$^x$.

When a tissue has been invaded by a microorganism or has been damaged, white blood cells, also called leukocytes, play a major role in the inflammatory response. One of the most important aspects of the inflammatory response involves the cell adhesion event. Generally, white blood cells are found circulating through the bloodstream. However, when a tissue is infected or becomes damaged, the white blood cells must be able to recognise the invaded or damaged tissue and be able to bind to the wall of the capillary near the affected tissue and diffuse through the capillary into the affected tissue. E-selectin helps two particular types of white blood cells recognise the affected sites and bind to the capillary wall so that these white blood cells may diffuse into the affected tissue.

There are three main types of white blood cells: granulocytes, monocytes and lymphocytes. Of these categories, E-selectin recognises sLe$^x$ presented as a glycoprotein or glycolipid on the surface of monocytes and neutrophils. Neutrophils are a subclass of granulocytes that phagocytise and destroy small organisms, especially bacteria. Monocytes, after leaving the bloodstream through the wall of a capillary, mature into macrophages that phagocytise and digest invading microorganisms, foreign bodies and senescent cells.

Monocytes and neutrophils are able to recognise the site where tissue has been damaged by binding to E-selectin, which is produced on the surface of the endothelial cells lining capillaries when the tissue surrounding a capillary has been infected or damaged. Typically, the production of E- and P-selectins is increased when the tissue adjacent to a capillary is infected. P-selectin is present constitutively in storage granules from which it can be rapidly mobilized to the cell surface after the endothelium has been activated. In contrast, E-selectin requires de novo RNA and protein synthesis, peak expression does not occur until about 4–6 hours after activation, and expression declines to basal levels after about 24–48 hours. White blood cells recognise affected areas because sLe$^x$ moieties present on the surface of the white blood cells bind to E- and P-selectin. This binding slows the flow of white blood cells through the bloodstream, since it mediates the rolling of leukocytes along the activated endothelium prior to integrin-mediated attachment and migration, and helps to localise white blood cells in areas of injury or infection.

While white blood cell migration to the site of injury helps fight infection and destroy foreign material, in many instances this migration can get out of control, with white blood cells flooding to the scene, causing widespread tissue damage. Compounds capable of blocking this process, therefore, may be beneficial as therapeutic agents. Thus, it would be useful to develop inhibitors that would prevent the binding of white blood cells to E- or P-selectin. For example, some of the diseases that might be treated by the inhibition of selectin binding to sLe$^x$ include, but are not limited to, ARDS, Crohn's Disease, septic shock, traumatic shock, multi-organ failure, autoimmune diseases, asthma, inflammatory bowel disease, psoriasis, rheumatoid arthritis and reperfusion injury that occurs following heart attacks, strokes and organ transplants. In addition to being found on some white blood cells, sLe$^a$, a closely related regiochemical isomer of sLe$^x$, is found on various cancer cells, including lung and colon cancer cells. It has been suggested that cell adhesion involving sLe$^a$ may be involved in the metastasis of certain cancers and that inhibitors of sLe$^a$ binding may be useful in the treatment of some forms of cancer.

As alluded to above, the ligands for the selectins generally consist of carbohydrate structures containing at least sialic acid, fucose and lactose. Lactose consists of galactose and glucose. Considering the obvious medical importance of selectin ligands, significant effort has been, and continues to be expended to identify the critical physical/chemical parameters associated with selectin ligands that enhance, or that are required for their activity. The majority of this work has centred around modifications to the natural ligands sLe$^x$, sLe$^a$ and variants thereof, as outlined in Ramphal et al, J. Med. Chem. (1996) 39:1357–1360. A range of carbohydrate mimics that retain the key functional units of the natural ligand have also been reported, by Ohmoto et al, J. Med. Chem. (1996) 39:1339–1343. More recently, some non-carbohydrate selectin ligands have been disclosed; see, for example, WO-A-9529681.

WO-A-9619231 discloses anti-inflammatory oligosaccharides of the type sugar-sugar-X-aglycone, wherein X is O, S, N or C.

Singh et al, J. Nat. Prod. (1990) 53(5): 1187–92, disclose the isolation of a weakly cytostatic natural product named aceratioside. It comprises a sugar moiety attached to the aromatic ring of a 1,2,3,4-tetrahydronaphthalene nucleus.

SUMMARY OF THE INVENTION

According to the present invention, compounds which are useful inhibitors of cell adhesion processes and may thus be useful in the treatment of inflammatory disorders (such as defined above) and certain cancers, are of formula I:

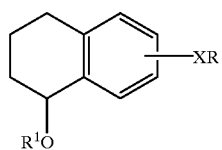

(I)

wherein R is selected from $CO_2H$, $SO_3H$, $CO_2R^2$, tetrazolyl and $NHSO_2CF_3$;

$R^1$ is fucose or mannose;

X is a bond, $C_{1-6}$ alkyl, $YC_{1-6}$ alkyl, Yheterocycloalkyl, $C_{2-6}$ alkyl interrupted by Y, $C_{2-6}$ alkenyl or $C_{2-6}$ alkynyl, and is attached to any available position on the benzene ring;

Y is O, $NR^3$, $S(O)_{0-2}$, CO, $CONR^3$, $NR^3CO$, $SO_2NR^3$ or $NR^3SO_2$;

$R^2$ is $C_{1-6}$ alkyl or benzyl; and $R^3$ is H or $C_{1-6}$ alkyl.

and the pharmaceutically-acceptable salts, esters, amides and prodrugs thereof.

Combinations of substituents and/or variables are only permissible if such combinations result in stable compounds.

DESCRIPTION OF THE INVENTION

It will be appreciated by those skilled in the art that compounds of formula (I) may contain one or more asymmetric centres. This invention relates to all possible chiral forms of compounds of formula (I) including mixtures of enantiomers, diastereomers and the like.

As used herein, the term "alkyl" means a straight chain or branched chain group of 1 to 6 carbon atoms including, but not limited to, methyl, ethyl, n-propyl, isopropyl, n-butyl, sec-butyl, isobutyl, tert-butyl and the like.

The term "alkenyl" means a straight chain or branched chain group of 2 to 6 carbon atoms including, but not limited to, ethenyl, propenyl, 1-butenyl, 2-methylpropenyl and the like. It will also be appreciated by those skilled in the art that alkenes may exist in E and Z geometric forms. The present invention relates to all possible E and Z geometric forms.

The term "alkynyl" means a straight chain or branched chain group of 2–6 carbon atoms including, but not limited to, ethynyl, propynyl, 1-butynyl, 3-methylbutyn-1yl and the like.

$CONR^3C_{1-6}$ alkyl means an $CON^3$-alkyl group in which the alkyl group is as previously described. Similarly, $COC_{1-6}$ alkyl means CO-alkyl, $OC_{1-6}$ alkyl means O-alkyl, $NR^3C_{1-6}$ alkyl means $NR^3$-alkyl, $NR^3COC_{1-6}$ alkyl means $NR^3CO$-alkyl and $NRSO^3SO_2C_{1-6}$ alkyl means $SO_2$-alkyl. Arylalkyl means an aryl-alkyl group in which alkyl is as described previously and aryl means a monocyclic or multicyclic carbocyclic radical containing about 6 to 10 carbon atoms.

Heterocycloalkyl means a ring of from 4 to 9 atoms where at least one atom is chosen from nitrogen, oxygen and sulphur. Such rings include, but are not limited to, pyrrolidine, piperidine, tetrahydropyran, tetrahydrofuran, piperazine and the like.

The term "pharmaceutically-acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of the compounds of the present invention. These salts can be prepared in situ during the final isolation and purification of the compounds or by separately reacting the purified compound it its free base form with a suitable organic or inorganic acid and isolating the salt thus formed. Representative salts include the hydrobromide, hydrochloride, sulfate, bisulfate, nitrate, acetate, oxalate, valerate, oleate, stearate, laurate, borate, benzoate, lactate, phosphate, tosylate, citrate, maleate, fumarate, succinate, tartrate, naphthylate, mesylate, glucoheptonate, lactiobionate, laurylsulphonate salts and the like. These may include cations based on the alkali and alkaline earth metals, such as sodium, lithium, potassium, calcium, magnesium and the like, as well as non-toxic ammonium, quaternary ammonium and amine cations including, but not limited to, ammonium, tetramethylammonium, tetraethylammonium, methylamine, dimethylamine, trimethylamine, triethylamine, ethylamine and the like. See, for example, Berge et al, "Pharmaceutical Salts" J. Pharm. Sci., 66:1–19 (1977), which is incorporated herein by reference.

Examples of pharmaceutically-acceptable, non-toxic esters of the compounds of this invention include $C_{1-6}$ alkyl esters wherein the alkyl group is a straight or branched chain. Acceptable esters also include $C_{5-7}$ cycloalkyl esters as well as arylalkyl esters such as, but not limited to benzyl. Esters of the compounds of the present invention may be prepared according to conventional methods.

Examples of pharmaceutically-acceptable, non-toxic amides of compounds of this invention include amides derived from ammonia, primary $C_{1-6}$ alkyl amines and secondary $C_{1-6}$ dialkyl amines, wherein the alkyl groups are straight or branched chain. In the case of secondary amines, the amine may also be in the form of a 5 or 6-membered heterocycle containing one nitrogen atom. Amides of the compounds of the invention may be prepared according to conventional methods.

The term "prodrug" refers to compounds, e.g. esters, that are rapidly transformed in vivo to yield the parent compound of the above formula, for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press (1987), both of which are incorporated herein by reference.

Compounds of general formula (I) may be prepared by any suitable method known in the art and/or by the following processes.

It will be appreciated that where a particular stereoisomer of formula (I) is required, the synthetic processes described herein may be used with the appropriate homochiral starting material and/or isomers may be resolved from mixtures using conventional separation techniques (e.g. HPLC).

The compounds according to the invention may be prepared by the following process. In the description and formulae below, the groups R, $R^1$, $R^2$, $R^3$, Y and X are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see "Protective Groups in Organic Synthesis", Wiley Interscience, T W Greene, PGM Wuts.

Compounds of the present invention as depicted by general formula (I) may be prepared from alcohols of general formula (II)

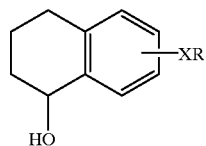

(II)

and sugars of general formula (m)

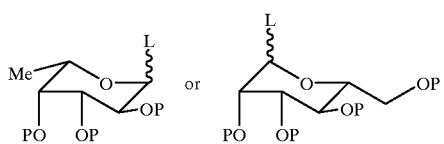

(III)

in which L is a suitable leaving group, such as a halogen (e.g. Br), and P is a suitable protecting group, such as an ether (e.g. benzyl ether) or an ester (e.g. acetate), followed by the removal of any suitable protecting groups.

Sugars of general formula (III) are either known compounds that may be commercially available, or can be readily prepared from commercially available starting materials using well known methods.

The alcohols of general formula (II) may be prepared by reduction of ketones of general formula (IV)

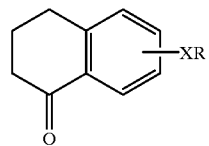

(IV)

using, for example, sodium borohydride in a suitable solvent, such as an alcohol (e.g. ethanol), at a temperature between 0° C. and the solvent reflux temperature, preferably at ambient temperature.

Compounds of general formula (IV) in which X is a $C_{2-6}$ alkenyl or $C_{2-6}$ alkynyl group can be prepared by palladium-catalysed couplings of the triflate (V)

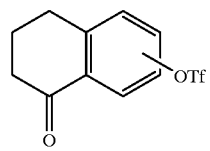

(V)

and the alkene $CH_2$=CH—$X^1R$ (VI) or alkyne CH≡C—$X^1R$ (VII), following the procedure of Chen & Yang, Tet. Lett. 27 1171 (1986), in which $X^1$ is $C_{2-4}$ alkyl optionally interrupted with Y.

Alkenes and alkynes of formulae (VI) and (VII) respectively, are either known compounds that may be commercially available or can be readily prepared from commercially available starting materials using methods known to those skilled in the art.

Compounds of formula (IV) in which X is $C_{1-6}$ alkyl optionally interrupted with Y, may be prepared by reduction of compounds of formula (IV) in which X is —CH=CH—$X^1R$ or —C≡C—$X^1R$ and $X^1$ is as defined above. Reductions of this type can be achieved using methods known to those skilled in the art, for example, by hydrogenation using hydrogen in the presence of a transition metal catalyst (e.g. palladium) in a suitable solvent, such as an alcohol (e.g. ethanol) at the appropriate temperature, preferably ambient temperature.

The compounds of formula (IV) in which X is $C_{1-6}$ alkyl optionally interrupted with Y, can be converted into compounds of formula (I) in which X is as described using the procedures (or modified variants thereof) described earlier.

Compounds of formula (IV) in which X is $CONR^3$—$C_{1-6}$ alkyl can be prepared from the carboxylic acid (VIII)

(VIII)

and the amine R—$C_{1-6}$ alkyl-$NHR^3$ (IX); the coupling reaction may be performed using standard conditions for amination reactions of this type. Thus, the reaction may be achieved in a solvent, for example an inert organic solvent such as an ether, e.g. a cyclic ether such as tetrahydrofuran, an amide e.g. a substituted amide such as dimethylformamide, or a halogenated hydrocarbon such as dichloromethane at a low temperature e.g. −30° C. to ambient temperature, such as −20° C. to 0° C., optionally in the presence of a base, e.g. an organic base such as an amine, e.g. triethylamine or a cyclic amine such as N-methylmorpholine. Where an acid of formula (VIII) is used, the reaction may additionally be performed in the presence of a condensing agent, for example a diimide such as N,-dicyclohexylcarbodiimide, advantageously in the presence of a triazole such as 1-hydroxybenzotriazole. Alternatively, the acid may be reacted with a chloroformate, for example ethyl chloroformate, prior to reaction with the amine of formula (IX).

Amines of general formula (IX) are either known compounds that may be commercially available or can be readily prepared from commercially available starting materials, using methods known to those skilled in the art.

The compounds of formula (IV) in which X is CONR$^3$—C$_{1-6}$ alkyl can be converted into compounds of formula (I) in which X is as described using the procedures (or modified variants thereof described earlier.

Acids of formula (VIII) can be prepared via hydrolysis of esters of formula (X)

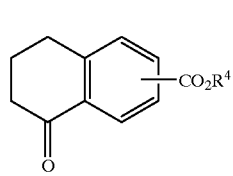

(X)

in which R$^4$ is alkyl (e.g. tert-butyl) using methods known to those skilled in the art.

Esters of formula (X) can be prepared from triflates of formula (V) using a palladium-catalysed carbonylation reaction. Ideally, the reaction is carried out in the presence of a palladium (II) catalyst (e.g. palladium acetate) under an atmosphere of carbon monoxide using an appropriate alcohol (e.g. methanol) as solvent in the presence of an organic base (e.g. triethylamine). Cosolvents that may facilitate the reaction, such as dimethylformamide, can also be added. The reaction may be undertaken at any temperature from ambient temperature to the reflux temperature of the solvent mixture, preferably at elevated temperatures.

Triflates of formula (V) may be prepared from alcohols of formula (XI)

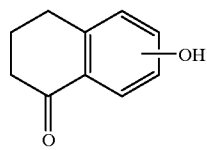

(XI)

using standard methods known to those skilled in the art. Alcohols of formula (XI) are either known compounds that may be commercially available or can readily be prepared from commercially available starting materials using methods known to those skilled in the art.

Compounds of formula (IV) in which X is OC$_{1-6}$ alkyl can be prepared by alkylation of alcohols of formula (XI) with compounds of formula Z—W—R (XII), in which Z is a leaving group such as a halogen (e.g. bromide) or a sulphonate ester (e.g. mesylate) and W is a C$_{1-6}$ alkyl group and R is as described previously. Such reactions can be undertaken in an appropriate solvent, such as an ether (e.g. tetrahydrofuran) or an amide (e.g. dimethylformamide) in the presence of a base such as sodium hydride or potassium carbonate at temperatures ranging from 0° C. to the solvent reflux temperature, preferably at ambient temperature.

Compounds of formula (XII) are either known compounds that may be commercially available or can be readily prepared from commercially available starting materials, using methods known to those skilled in the art.

The compounds of formula (IV) in which X is OC$_{1-6}$ alkyl can be converted into compounds of formula (I) in which X is as described using the procedures (or modified variants thereof) described earlier.

Compounds of formula (IV) in which X is COC$_{1-4}$ alkyl can be prepared from activated esters or amides (e.g. Weinreb amides) or acid halides of formula (XIII)

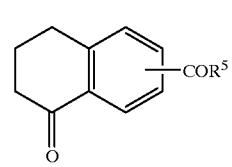

(XIII)

in which R$^5$ may be for example a halogen (e.g. chlorine) or an imidazole group, and compounds of formula M—W—R (XIV) in which M is a metal such as lithium or a Grignard reagent such as MgBr and W and R are as previously defined. It will be appreciated by those skilled in the art that reactions of this type may require protected forms of compounds of formula (XIII) as described in PGM Wuts et al, Protective Groups in Organic Synthesis, Wiley Interscience.

Compounds of formula (XIII) can be readily prepared from acids of formula (VII) using standard methods known to those skilled in the art. Compounds of formula (XIV) can be readily prepared from compounds of formula (XII) in which Y is a halogen atom, using standard methods known to those skilled in the art.

The compounds of formula (IV) in which X is COC$_{1-6}$ alkyl can be converted into compounds of formula (I) in which X is as described using the procedures (or modified variants thereof) described earlier.

Compounds of general formula (IV) in which X is a NR$^3$C$_{1-6}$ alkyl, NR$^3$COC$_{1-6}$ alkyl or NR$^3$SO$_2$C$_{1-6}$ alkyl group may be prepared from an amine of formula (XV)

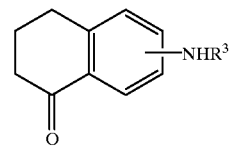

(XV)

or a protected derivative thereof, and a compound of formula R$^6$—W—R (XVI) where R$^6$ is a carboxylic acid, acid chloride or mixed anhydride, a sulphonyl chloride, aldehyde, halogen (e.g. bromide) or sulphonate ester (e.g. mesylate), using standard methods known to those skilled in the art. In compounds of formula (XVI), W and R are as described above, except that when R$^6$ is aldehyde, W is C$_{2-6}$ alkyl.

The compounds of formula (IV) in which X is a NR$^3$—C$_{1-6}$ alkyl, NR$^3$COC$_{1-6}$ alkyl or NR$^3$SO$_2$C$_{1-6}$ alkyl group may be converted into compounds of formula (I) in which X is as described using the procedures (or modified variants thereof) described earlier.

Compounds of formula (XV) and (XVI) are either known compounds that may be commercially available or can be readily prepared from commercially available starting materials using methods known to those skilled in the art.

Intermediates of general formulae (II)–(XVI) may be obtained in optically pure or racemic form. In the chiral form, they provide asymmetric building blocks for the enantiospecific synthesis of compounds of general formula (I). Also, any mixtures of final products or intermediates obtained can be separated on the basis of the physicochemical differences of the constituents, in a known manner, into the pure final products or intermediates, for example by chromatography, distillation, fractional crystallisation, or by formulation of a salt if appropriate or possible under the circumstances.

The present invention also provides a method for treating diseases such as ARDS, septic shock, traumatic shock, multi-organ failure, Crohn's disease, ulcerative colitis, intestinal graft vs host disease, inflammatory bowel disease; ischemia reperfusion injury caused by myocardial infarction, cerebral ischemic event (e.g. stroke), renal, hepatic and splenial infarction, brain surgery, cardiac surgery (e.g. coronary artery bypass), elective angioplasty and the like; rheumatoid arthritis, osteoarthritis, systemic lupus erythematosus, multiple sclerosis, meningitis, encaphalitis, type I diabetes, uvietis, psoriasis, atopic dermatitis, allergic contact dermatitis, delayed type hypersensitivity reaction, asthma, anaphylaxis, allergic rhinitis and ocular inflammation. In addition to the above human uses, it is contemplated that these compounds can be used in veterinary uses to treat related diseases.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically-acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified above. Sweetening, flavouring and colouring agents may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example gycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above-indicated conditions (about 2.5 mg to about 7 gms per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy.

The following Examples illustrate the preparation of compounds of Formula (I), and as such are not intended to limit the invention as set forth in the claims.

In the Examples, the following abbreviations are used:

| DMAP | A-dimethylaminopyridine |
| --- | --- |
| dppp | bis(diphenylphosphinyl)propane |
| DMF | N,N-dimethylformamide |
| TEABr | tetraethylammonium bromide |
| THF | tetrahydrofuran |
| DCC | dicyclohexyl carbodiimide |
| EtOAC | ethyl acetate |
| TBAF | tetrabutylammonium fluoride |

INTERMEDIATE 1

7-Hydroxy-1,2,3,4-tetrahydronalphthalen-1-one

A mixture of 7-methoxytetralone (18 g), glacial acetic acid (40 ml) and concentrated HBr (100 ml) was heated at reflux for 6 h. The mixture was cooled, water (600 ml) was added and the precipitate filtered. The crude product was filtered through silica gel using ethyl acetate as solvent and recrystallised from methanol/water(1:3) to yield the title compound as a yellow solid (6.29 g).

Mass spec m/z 162 (M$^+$)

INTERMEDIATE 2

7-Trifluoromethanesulphonyloxy-1,2,3,4-tetrahydronaphthalen-1-one

Trifluoromethanesulphonic anhydride (10 g) was added dropwise over 30 mins. to a mixture of Intermediate 1 (4.8 g), DMAP (0.93 g) and 2,6-lutidine (3.8 g) in dichloromethane (250 ml) at −50° C. The reaction mixture was allowed to warm to room temperature and stirred for 18 h. The mixture was washed with water (100 ml), 2% sodium hydroxide solution (200 ml), 10% potassium hydrogen sulphate solution (200 ml) and water (100 ml). The organic phase was dried (MgSO$_4$) and concentrated it, vacuo to give the title compound as a red solid (8.3 g).

Mass spec m/z 294 (M$^+$)

INTERMEDIATE 3

7-Methoxycarbonyl-1,2,3,4-tetrahydronaphthalen-1-one

A suspension of Intermediate 2 (1.47 g), triethylamine (1.3 ml), palladium acetate (36 mg) and dppp (62 mg) in methanol (5 ml) and DMF (10 ml) was heated under an atmosphere of carbon monoxide at 70° C. for 3 h. The reaction mixture was cooled and partitioned between water (50 ml) and ether (50 ml). The aqueous layer was extracted with ether (3×50 ml) and the combined organic layers were dried (MgSO$_4$) and concentrated in vacuo to give the title compound as a red oil (0.97 g).

Mass spec m/z 204 (M$^+$)

INTERMEDIATE 4

7-Methoxycarbonyl-1,2,3,4-tetrahydro-1-naphthol

Sodium borohydride (0.15 g) was added to a solution of Intermediate 3 (0.97 g) in methanol (20 ml) at room temperature. The mixture was stirred for 2 h then concentrated in vacuo. The residue was partitioned between ether (3×30 ml) and water (30 ml). The organic layers were dried (MgSO$_4$) and concentrated in vacuo, and the residue was purified by column chromatography (Et$_2$O:petrol 1:10) to give the title compound as a yellow oil (0.80 g).

Mass spec m/z 206 (M$^+$)

INTERMEDIATE 5

Ethyl 2,3,4-tri-O-benzyl-1-thio-L-fucopyranose

L-Fucose (10 g) was treated with acetic anhydride/pyridine (300 ml, 2:1) at 100° C. for 3 h. The solution was cooled, concentrated in vacuo and azeotroped with xylene (2×50 ml). The residue was dissolved in dichloromethane (300 ml) and tin (IV) chloride (3 ml) and ethanethiol (6 ml) were added at 0° C. The mixture was warmed to room temperature and stirred for 18 h. The solution was washed with 10% sulphuric acid (20 ml), saturated sodium bicarbonate (20 ml) and water (20 ml), dried (MgSO$_4$) and concentrated in vacuo. The residue was dissolved in methanol (50 ml) and sodium methoxide in methanol (0.3 g Na/50 ml MeOH) was added. The solution was stirred for 2 h, concentrated in vacuo and the residue dissolved in DMF (150 ml). The solution was cooled to 0–5° C. and sodium hydride (60%, 14.7 g) was added. The mixture was stirred for 1 h, benzyl bromide (32 ml) was added and the mixture was stirred for 18 h. Methanol (20 ml) was added and the mixture was partitioned between toluene and water. The organic phase was washed with water (20 ml), dried (MgSO$_4$) and concentrated in vacuo. The residue was purified by flash chromatography (ethyl acetate:petrol 1:20) to give the title compound as a colourless solid (17.9 g).

Mass spec m/z 496 (M+NH$_4$)

INTERMEDIATE 6

1-[7-Methoxycarbonyl-1,2,3,4-tetrahydro-1(R,S)-naphthyl]-2,3,4-tri-O-benzyl-α-L-fucopyranose Bromine (0.1 ml) was added dropwise to a solution of Intermediate 5 (0.89 g) in dichloromethane (12 ml) at 0° C.

The solution was stirred for 20 min at 0° C. then concentrated in vacuo. The residue was dissolved in dichloromethane (3 ml) and the solution was added to a mixture of Intermediate 5 (0.31 g), TEABr (0.39 g) and 4 Å molecular sieves (2 g) and the resultant mixture was stirred at room temperature for 24 h. The suspension was filtered through Celite and the organic filtrate was washed with sodium bicarbonate (20 ml), and water (20 ml), dried (MgSO$_4$) and concentrated in vacuo. The residue was purified by flash chromatography (ethyl acetate:petrol 1:9) to give the title compound as a colourless oil (0.57 g).

Mass spec n/z 640 (M+NH$_4$)

INTERMEDIATE 7

1-[7-Carboxy-1,2,3,4-tetrahydro-1(R,S)-naphthyl]-2,3,4-tri-O-benzyl-α-L-fucopyranose Lithium hydroxide (0.15 g) was added to a solution of Intermediate 6 (0.32 g) in THF-water (5 ml, 4:1). The solution was heated at reflux for 3 h, the THF was evaporated in vacuo, water (10 ml) was added and the aqueous layer adjusted to pH7 using potassium orthophosphate. The aqueous mixture was extracted with ethyl acetate (4×25 ml), and the extracts were dried (MgSO$_4$) and concentrated in vacuo to give the title compound as a yellow oil (0.29 g).

Mass spec m/z 626 (M+NH$_4$)

General procedures for the reaction of Intermediate 7 with amines are:

A. The acid (9) (1.0 eq), DCC (1.1 eq) and DMAP (0.1 eq) were dissolved in dichloromethane and the appropriate amino acid benzyl ester, p-toluenesulfonate or hydrochloride salt (1.1 eq) was added followed by triethylamine (1.1 eq). The mixture was stirred overnight. The product was filtered and the solvent removed and the residue was subjected to silica gel chromatography (EtOAc/Petroleum ether gradient, 1:10–5:10) and gave the product.

B. The acid (9), BOP-Cl (1.2 eq) and the appropriate amino acid, benzyl ester, p-toluenesulfonate or hydrochloride salt (1.1 eq) were added to dichloromethane and the mixture was stirred at room temperature. Then triethylamine (2.0 eq) was added dropwise over 30 mins and the mixture was stirred for 2 h. The solvent was removed and the residue chromatographed ((EtOAc/Petroleum ether gradient, 1:10–5:10) and gave the product.

INTERMEDIATE 8

1-[7-[((S)-N-1-Benzyloxycarbonylethyl)aminocarbonyl]-1,2,3,4-tetrahydro-1(R,S)-naphthyl]-2,3,4-tri-O-benzyl-α-L-fucopyranose Prepared using procedure A.

Mass spec m/z 770 (M+NH$_4$)

INTERMEDIATE 9

1-[7-[((R)-N-1-Benzyloxycarbonylethyl)aminocarbonyl]-1,2,3,4-tetrahydro-1(R,S)-naphthyl]-2,3,4-tri-O-benzyl-α-L-fucopyranose Prepared using procedure A.

Mass spec m/z 770 (M+NH$_4$)

INTERMEDIATE 10

1-[7-[(N-Benzyloxycarbonylmethyl)aminocarbonyl]-1,2,3,4-tetrahydro-1(RS)-naphthyl]-2,3,4-tri-O-benzyl-α-L-fucopyranose Procedure B using glycine benzyl ester, hydrochloride salt and the acid (0.15 g, 0.25 mmol) in CH$_2$Cl$_2$(2 mL) gave the title compound (0.125 g).

IR Vmax 3282, 1757, 1631 cm$^{-1}$

INTERMEDIATE 11

1-[7-[[2-(S)-Benzyloxycarbonylpyrrolin-1-yl]carbonyl]-1,2,3,4-tetrahydro-1(RS)-naphthyl]-α-L-fucopyranose Procedure A using L-proline benzyl ester provided the title compound.

Mass spec n/z 796 (M+H)

INTERMEDIATE 12

7-(4-Hydroxy-1-butynyl)-1,2,3,4-tetrahydronaphthalen-1-one

A mixture of Intermediate 2 (0.96 g), Pd (II)Cl$_2$(PPh$_3$)$_2$ (63 mg), triethylamine (1.8 ml) and but-3-yn-1-ol (0.35 g) in DMF (7 ml) was stirred at 70° C. for 18 h. The mixture was cooled, ethyl acetate (20 ml) was added and the mixture was washed with saturated ammonium chloride (2×20 ml) and water (2×20 ml). The organic phase was dried (MgSO$_4$) and concentrated in vacuo and the residue was purified by flash chromatography (ether:petrol (1:1)) to give the title compound as a colourless solid (0.58 g).

Mass spec m/z 214 (M$^+$)

INTERMEDIATE 13

7-(4-Hydroxybutyl)-1,2,3,4-tetrahydronaphthalen-1-one

10% Pd/C (30 mg) was added to a solution of Intermediate 12 (0.3 g) in ethanol (5 ml) and the suspension was stirred under a hydrogen atmosphere for 1 h. The suspension was filtered through Celite and the filtrate was concentrated in vacuo. The residue was purified by flash chromatography (EtOAc:petrol 1:2) to give the title compound as a pale yellow oil (0.21 g).

Mass spec m/z 218 (M$^+$)

INTERMEDIATE 14

7-(3-Carboxypropyl)-1,2,3,4-tetrahydronaphthalen-1-one

Jones reagent (1.6 ml) was added dropwise over 30 min to Intermediate 13 (0.52 g) at 0° C. The mixture was stirred at ambient temperature for 2 h, propan-2-ol (0.5 ml) was added and the mixture was stirred for a further 30 mins. The pH was adjusted to 4 by addition of solid sodium bicarbonate. Ether (20 ml) was added and the organic phase was extracted with 5% sodium carbonate solution (4×30 ml). The aqueous extracts were acidified to pH1 with 5% HCl then extracted with ether (3×30 ml). The organic extracts were dried (MgSO$_4$) and concentrated in vacuo to give the title compound as a dark brown oil (0.23 g).

Mass spec m/z 232 (M$^+$)

INTERMEDIATE 15

7-[3-(Benzyloxycarbonyl)propyl]-1,2,3,4-tetrahydronaphthalen-1-one

A solution of Intermediate 14 (0.39 g), benzyl alcohol (0.39 g), DCC (0.35 g) and DMAP (20 mg) in dichloromethane (10 ml) was stirred at ambient temperature for 18 h. The mixture was filtered, the filtrate was concentrated in vacuo and the residue purified by flash chromatography (EtOAc:petrol, 3: 10) to give the title compound as a colourless oil (0.48 g).

Mass spec m/z 322 (M+)

INTERMEDIATE 16

7-[3-(Benzyloxycarbonyl)propyl]-1,2,3,4-tetrahydro-1(RS)-naphthol

The title compound (0.39 g) was prepared from Intermediate 15 (0.49 g) using the procedure described for the preparation of Intermediate 4.

Mass spec m/z 324 (M+)

INTERMEDIATE 17

1-[7-[3-(Benzyloxycarbonyl)propyl]-1,2,3,4-tetrahydro-1 (R,S)-naphthol]-2,3,4-O-benzyl-α-L-fucopyranose The title compound (0.37 g) was prepared from Intermediate 16 (0.39 g) using the procedure described to prepare Intermediate 6.

Mass spec m/z 758 (M+NH$_4$)

INTERMEDIATE 18

2,2-Dimethylbut-3-ynoic acid, benzyl ester

The title compound (0.33 g) was prepared from 2,2-dimethylbut-3-ynoic acid using the procedure described for the preparation of Intermediate 15.

CHN analysis Found: C, 77.2; H, 6.9% $C_{13}H_{14}O_2$ requires: C, 77.0; H, 7.0%

INTERMEDIATE 19

7-[3-(Benzyloxylcarbonyl)-2,2-dimethyl-1-butynyl]-1,2,3,4-tetrahydronaphthalen-1-one The title compound (0.58 g) was prepared from Intermediate 18 using the procedure outlined for the preparation of Intermediate 12.

IR Vmax 1739 cm$^{-1}$, 1691 cm$^{-1}$

INTERMEDIATE 20

7-[3-(Benzyloxycarbonyl)-2,2-dimethyl-1-butynyl]-1,2,3,4-tetrahydro-1(RS)-naphthol The title compound (0.36 g) was prepared from Intermediate 19 using the procedure outlined for the preparation of Intermediate 4.

Mass spec m/z 366 (M+NH$_4$)

INTERMEDIATE 21

1-[7-[3-Benzyloxycarbonyl-2,2-dimethyl-1-butynyl]-1,2,3,4-tetrahydro-1(RS)-naphthyl]-2,3,4-tri-O-benzyl-α-L-fucopyranose The title compound (0.19 g) was prepared from Intermediate 20 using the procedure outlined for the preparation of Intermediate 6.

Mass spec m/z 782 (M+NH$_4$)

INTERMEDIATE 22

7-tert-Butyldimethylsilyloxy-1,2,3,4-tetrahydronphthalen-1-one

A solution of 7-hydroxytetralone (0.20 g), tert-butyldimethylsilyl chloride (0.19 g) and imidazole (0.20 g) in DMF (10 ml) was stirred at ambient temperature for 18 h. The mixture was partitioned between EtOAc and water. The aqueous layer was extracted with EtOAc (3×20 ml) and the combined organic layers were washed with water (30 ml), dried (MgSO$_4$) and concentrated in vacuo. The residue was purified by flash chromatography (ether:petrol 1:10) to give the title compound as a colourless oil (0.33 g)

Mass spec m/z 277 (M+H)

INTERMEDIATE 23

7-tert-Butyldimethylsilyloxy-1,2,3,4-tetrahydro-1-naphthol

The title compound (0.24 g) was prepared from Intermediate 22 using the procedure described for the preparation of Intermediate 4.

Mass spec m/z 278 (M+)

INTERMEDIATE 24

1-[7-tert-Butyldimethylsilyloxy-1,2,3,4-tetrahydro-1 (R,S)-naphthyl]-2,3,4-tri-O-benzyl-α-L-fucopyranose Prepared from Intermediate 22 using the procedure described for Intermediate 6.

Mass spec m/z 712 (M+NH$_4$)

INTERMEDIATE 25

1-[7-tert-Butyldimethylsilyloxy-1,2,3,4-tetrahydro-1 (R,S)-naphthyl]-2,3,4-tri-O-acetyl-α-L-fucopyranose 5% Pd—C (300 mg) was added to a solution of Intermediate 24 (0.91 g) in ethanol (10 ml). The suspension was stirred under a hydrogen atmosphere for 5 h, then filtered through Celite. The filtrate was concentrated in vacuo and the residue was dissolved in pyridine (5 ml). Acetic anhydride (5 ml) and DMAP (10 mg) were added and the solution was stirred at ambient temperature for 24 h. Water (20 ml) was added and the mixture was extracted with ethyl acetate (3×20 ml). The combined organic layers were washed with potassium hydrogen sulphate (10%, 20 ml), saturated sodium bicarbonate (20 ml) and water (10 ml), dried (MgSO$_4$) and concentrated in vacuo. The residue was purified by flash chromatography (EtOAc:petrol 1:1) to give the title compound as a yellow oil (0.72 g).

Mass spec n/z 568 (M+NH$_4$)

INTERMEDIATE 26

1-[7-Trifluoromethanesulphonyloxy-1,2,3,4-tetrahydro-1(R,S)-naphthyl]-2,3,4-tri-O-acetyl-α-L-fucopyranose A solution of Intermediate 25 (0.72 g) in THF (25 ml) was cooled to 0° C. TBAF (1M, 3 ml) was added and stirring at 0° C. was continued for 30 min. The reaction mixture was concentrated in vacuo and the residue was dissolved in dichloromethane (10 ml) and cooled to −20° C. 2,6-Lutidine (0.22 g), DMAP (27 mg) and trifluoromethanesulphonic anhydride (0.06 g) were added and the mixture was stirred at −20° C.–20° C. for 24 h. Water (20 ml) was added and the mixture was extracted with EtOAc (3×20 ml). The combined extracts were washed with potassium hydrogen sulphate (30 ml), sodium bicarbonate (25 ml) and water (20 ml), dried (MgSO$_4$) and concentrated in vacuo. The residue was purified by flash chromatography (EtOAc:petrol 1:1) to give the title compounds as an orange oil (0.54 g).

Mass spec m/z 586 (M+NH$_4$)

INTERMEDIATE 27

1-[7-[3'-Benzyloxycarbonyl-2',2'-dimethyl-1'-butynyl]-1,2,3,4-tetrahydro-1(R,S)-naphthyl]-2,3,4-tri-O-acetyl-α-L-fucopyranose The title compound (0.09 g) was prepared from Intermediate 26 using the procedure described for the preparation of Intermediate 12.

Mass spec n/z 638 (M+NH$_4$)

EXAMPLE 1

1-[7-((S)-N-1-Carboxyethylaminocarbonyl)-1,2,3,4-tetrahydro-1(R,S)-naphthyl]-α-L-fucopyranose 5% Pd—C (240 mg) was added to a solution of Intermediate 8 (240 mg) in ethanol (5 ml). The suspension was stirred under a hydrogen atmosphere at ambient temperate for 6 h. The mixture was filtered through Celite, the solvent was evaporated in vacuo and the residue was purified by flash chromatography (methanol) to give the title compound as a white solid (0.12 g).

Mass spec m/z 432 (M+Na)

IR Vmax (KBr) 3404 cm$^{-1}$, 1728 cm$^{-1}$, 1636 cm$^{-1}$

The following compounds were prepared using the procedure described for Example 1, from Intermediates 9, 7, 17, 21, 10 and 11, respectively.

EXAMPLE 2

1-[7-((R)-N-1-Carboxyethylaminocarbonyl)-1,2,3,4-tetrahydro-1(R,S)-naphthyl]-α-L-fucopyranose Mass spec m/z 432 (M+Na)

TLC R$_f$=0.35 [MeOH:EtOAc(1:1)]

EXAMPLE 3

1-[7-Carboxy-1,2,3,4-tetrahydro-1(R,S)-naphthyl]-α-L-fucopyranose

Mass spec m/z 361 (M+Na)

TLC R$_f$=0.1 [EtOAc:MeOH (5:1)]

EXAMPLE 4

1-[7-(3-Carboxypropyl)-1,2,3,4-tetrahydro-1(R,S) naphthyl]-α-L-fucopyranose

Mass spec m/z 403 (M+Na)

δ$_H$ (acetone-d6/D$_{2O}$) 7.46 (1H,br.s), 7.17–7.22 (5H, m); 5.33 (1H,d ); 5.25 (1H, d); 4.80 (2H, m); 4.23 and 4.25 (2H, 2xq); 4.00–3.84 (6H, m); –2.87–2.71 (4H, m); –2.73 (4H, t); 2.41 (4H, t); 2.10–1.86 (12H, m); 1.44 (3h, d) and 1.38 (3H, d).

EXAMPLE 5

1-[7-[3-Carboxy-2,2-dimethyl-1-propyl]-1,2,3,4-tetrahydro-1(R,S)-naphthyl]-α-L-fucopyranose Mass spec ml/z 426 (M+NH$_4$)

IR Vmax (KBr) 3433 cm$^{-1}$, 1701 cm$^{-1}$

EXAMPLE 6

1-[7-[(N-carboxymethyl)aminocarbonyl]-1,2,3,4-tetrahydro-1(R,S)-naphthyl]-α-L-fucopyranose IR Vmax (KBr) 3406, 1727, 1638 cm$^{-1}$ Mass spec m/z 418 (M+Na).

EXAMPLE 7

1-[7-[[2-(S)-carboxypyrrolidin-1-yl]carbonyl]-1,2,3,4-tetrahydro-1(R,S)-naphthyl]-α-L-fucopyranose TLC Rf 0.1 (1:1 EtOAc:methanol)

Mass spec m/z 458 (M+Na)

EXAMPLE 8

1-[7-[3-Carboxy-2,2-dimethyl-1-propynyl]-1,2,3,4-tetrahydro-1(R,S)-naphthyl]-α-L-fucopyranose Sodium methoxide in methanol (2 ml of a 0.6 g Na/100 ml MeOH solution) was added to a stirred solution of Intermediate 27 (0.12 g) in methanol (2 ml) at ambient temperature. The solution was stirred for 1 h, water (15 ml) was added and potassium hydrogen phosphate was added until the pH=7. The mixture was concentrated in vacuo and the residue was purified by flash chromatography (EtOAc:MeOH 1:1) gave the title compound as a white solid (38 mg).

Mass spec m/z 427 (M+Na)

δ$_H$ (acetone d6D2O) 7.59 (1H, br.s), 7.38 (1H, br.s), 7.36 and 7.30 (2H, 2xd), 7.13 and 7.10 (2H, 2xq), 5.23 (1H, br.s), 5.19 (1H, d), 4.68 (2H, br.s), 4.16 and 4.07 (2H, 2xq), 3.87–3.76(6H, m), 2.85 (4H, m), 2.10–1.70 (8H, m), 1.51 (6H, s), 1.35 (3H,d) and 1.29 (3H,d).

Assay

After 4 hours' stimulation of HUVEC by TNFα, in the presence or in the absence of drug, cells were washed, and fluorescent dye-labelled HL60 cells were added to UVEC for 30 min at 37° C., always in the presence or in the absence of drug. At the end of incubation, HUVEC were washed three times to remove non-adherent HL60 cells. Spectrofluorimetric measurements were performed with a multiple reader (Cytofluor 2350, Millipore).

Alternatively, 96-well plates were coated with 2 pg/ml recombinant E-selectin solution and ten blocked with 1% (w/v) bovine serum albumin in PBS. Wells were washed with PBS and blotted dry. HL-60 cells were resuspended in serum-free medium and added to each well at a final density of 4×10$^6$/ml in the presence and absence of drug. Plates were incubated for 1 h at 37° C. in an atmosphere of 5% CO$_2$, then non-adherent cells were washed off with PBS containing calcium and magnesium. Fresh medium was added to all wells and the number of adherent cells per well was quantified using a colorimetric method.

What is claimed is:

1. A compound of the formula

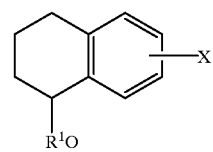

(I)

wherein
- R$^1$ is selected from the group consisting of fucose and mannose;
- X is selected from the group consisting of R, C$_{1-6}$ alkyl substituted with R, YC$_{1-6}$ alkyl substituted with R, Yheterocycloalkyl, substituted with R, C$_{2-6}$ alkyl substituted with R interrupted by Y, C$_{2-6}$ alkenyl substituted with R, and C$_{2-6}$ alkynyl substituted with R;

R is selected from the group consisting of $CO_2H$, $SO_3H$, $CO_2R^2$, tetrazolyl, and $NHSO_2CF_3$;

Y is selected from the group consisting of O, $NR^3$, $S(O)_{0-2}$, CO, $CONR^3$, $NR^3CO$, $SO_2NR^3$, and $NR^3SO_2$;

$R^2$ is selected from the group consisting of $C_{1-6}$ alkyl and benzyl; and $R^3$ is selected from the group consisting of H and $C_{1-6}$ alkynyl;

or a pharmaceutically-acceptable, salt, ester, amide, or prodrug thereof.

2. The compound according to claim 1, wherein Y is selected from the group consisting of $CONR^3$, CO, $SO_2NR^3$, SO, and $SO_2$.

3. The compound according to claim 1, wherein X is selected from the group consisting of R, $C_{1-6}$ alkyl substituted with R, $YC_{1-6}$ alkyl substituted with R, $C_{2-6}$ alkyl substituted with R interrupted by Y, $C_{2-6}$ alkenyl substituted with R, and $C_{2-6}$ alkynyl substituted with R.

4. The compound according to claim 3, wherein X is selected from the group consisting of R, $C_{1-6}$ alkyl substituted with R, $YC_{1-6}$ alkyl substituted with R, $C_{2-6}$ alkenyl substituted with R and $C_{2-6}$ alkynyl substituted with R.

5. The compound according to claim 1, wherein $R^1$ is fucose.

6. The compound according to claim 3, wherein $R^1$ is fucose.

7. The compound according to claim 1, selected from the group consisting of

1-[7-((S)-N-1-carboxyethylaminocarbonyl)-1,2,3,4-tetrahydro-1-naphthyl]-α-L-fucopyranose;

1-[7-((R)-N-1-carboxyethylaminocarbonyl)-1,2,3,4-tetrahydro-1-naphthyl]-α-L-fucopyranose;

1-[7-carboxy-1,2,3,4-tetrahydro-1-naphthyl]-α-L-fucopyranose;

1-[7-(3-carboxypropyl)-1,2,3,4-tetrahydro-1-naphthyl]-α-L-fucopyranose;

1-[7-(3-carboxy-2,2-dimethyl-1-butyl)-1,2,3,4-tetrahydro-1-naphthyl]-α-L-fucopyranose;

1-[7-(N-carboxymethyl)aminocarbonyl)-1,2,3,4-tetrahydro-1-naphthyl]-α-L-fucopyranose;

1-[7-[[2-(S)-carboxypyrrolidin-1-yl]carbonyl]-1,2,3,4-tetrahydro-1-naphthyl]-α-L-fucopyranose; and 1-[7-[3-carboxy-2,2-dimethyl-1-butynyl]-1,2,3,4-tetrahydro-1-naphthyl]-α-L-fucopyranose.

8. A pharmaceutical composition for therapeutic use, comprising a compound of claim 1 and a carrier or diluent.

9. A method for treating a human or animal having a selectin-mediated cell adhesion condition, wherein said method comprises administering to a human or animal a therapeutic amount of a compound of claim 1, or a pharmaceutical composition thereof, that is effective for treating said selectin-mediated cell adhesion condition.

10. The method according to claim 9, wherein said condition is selected from the group consisting of ARDS, an inflammatory bowel disease, psoriasis, rheumatoid arthritis, and reperfusion injury.

11. The method according to claim 9, wherein said condition is selected from the group consisting of septic shock, traumatic shock, multiorgan failure; ischaemic reperfusion injury; cerebral ischaemia; renal, hepatic, or splenial infarction; brain surgery; cardiac surgery; elective angioplasty; systemic lupus erythematosus; multiple sclerosis; meningitis; encephalitis; psoriasis; atopic dermatitis; allergic contact dermatitis; delayed-type hypersensitive reaction; uveitis; allergic rhinitis; ocular inflammation; Crohn's disease; ulcerative colitis; and osteoarthritis.

12. The method according to claim 9, wherein said condition is asthma.

* * * * *